US011883992B2

(12) United States Patent
Kozuka

(10) Patent No.: US 11,883,992 B2
(45) Date of Patent: Jan. 30, 2024

(54) MOLDING SUPPORT DEVICE FOR INJECTION MOLDING MACHINE

(71) Applicant: NISSEI PLASTIC INDUSTRIAL CO., LTD., Nagano-ken (JP)

(72) Inventor: Makoto Kozuka, Hanishina-gun (JP)

(73) Assignee: NISSEI PLASTIC INDUSTRIAL CO., LTD., Nagano-ken (JP)

(*) Notice: Subject to any disclaimer, the term of this patent is extended or adjusted under 35 U.S.C. 154(b) by 783 days.

(21) Appl. No.: 16/976,674

(22) PCT Filed: Mar. 25, 2019

(86) PCT No.: PCT/JP2019/012533
§ 371 (c)(1),
(2) Date: Aug. 28, 2020

(87) PCT Pub. No.: WO2019/188998
PCT Pub. Date: Oct. 3, 2019

(65) Prior Publication Data
US 2021/0001528 A1 Jan. 7, 2021

(30) Foreign Application Priority Data
Mar. 27, 2018 (JP) ................................ 2018-059226

(51) Int. Cl.
B29C 45/78 (2006.01)
G01N 25/02 (2006.01)
G01N 33/44 (2006.01)

(52) U.S. Cl.
CPC ............. B29C 45/78 (2013.01); G01N 25/02 (2013.01); G01N 33/442 (2013.01);
(Continued)

(58) Field of Classification Search
CPC .......... B29C 45/78; B29C 2945/76187; B29C 2945/76193; B29C 2945/76354; B29C 2945/76531; G01N 25/02; G01N 33/442
(Continued)

(56) References Cited

U.S. PATENT DOCUMENTS

2016/0288392 A1* 10/2016 Maruyama ............ B29C 45/762
2019/0389112 A1* 12/2019 Collins .................... B29C 45/03
2020/0198201 A1* 6/2020 Shimokusuzono ..... B29C 45/78

FOREIGN PATENT DOCUMENTS

JP 2005-22260 A 1/2005
JP 2007-76328 A 3/2007
(Continued)

OTHER PUBLICATIONS

International Search Report, issued in PCT/JP2019/012533, dated Jun. 11, 2019.

Primary Examiner — Aditya S Bhat
(74) Attorney, Agent, or Firm — Birch, Stewart, Kolasch & Birch, LLP

(57) ABSTRACT

Provided are a basic data input unit to input basic data including molding conditions data related to molding conditions and screw data related to the form of the screw; a calculation formula data setting unit to set solid phase rate calculation formula data to calculate the solid phase rate of the molten resin in a heating cylinder based on this basic data; a calculation processing function unit having a solid phase rate calculation processing unit to use calculation processing based on the basic data and the solid phase rate calculation formula data to calculate an estimated solid phase rate of the molten resin at the measurement completion; and an output processing function unit that performs display processing to display information related to the estimated solid phase rate on a display.

9 Claims, 8 Drawing Sheets

(52) U.S. Cl.
CPC ............... *B29C 2945/76187* (2013.01); *B29C 2945/76193* (2013.01); *B29C 2945/76354* (2013.01); *B29C 2945/76531* (2013.01)

(58) Field of Classification Search
USPC .......................................................... 702/30
See application file for complete search history.

(56) References Cited

FOREIGN PATENT DOCUMENTS

| | | |
|---|---|---|
| JP | 2015-123668 A | 7/2015 |
| JP | 2017-165028 A | 9/2017 |
| JP | 2017-209880 A | 11/2017 |
| WO | WO 2018/155230 A1 | 8/2018 |

* cited by examiner

ADHESION EASINESS

| METAL OF SCREW SURFACE | RESIN TYPE | | | | |
|---|---|---|---|---|---|
| | PP | POM | ABS | GPPS | LDPE |
| Cr | 1 | 2 | 3 | 4 | 2 |
| CrN | 2 | 3 | 4 | 4 | 1 |
| TiN | 3 | 1 | 2 | 4 | 2 |
| TiC | 4 | 2 | 1 | 4 | 3 |

| METAL OF SCREW SURFACE | DECOMPOSITION RESIN TYPE | | | | |
|---|---|---|---|---|---|
| | PP | POM | ABS | GPPS | LDPE |
| Cr | 1 | 1 | 1 | 1 | 1 |
| CrN | 2 | 2 | 2 | 2 | 2 |
| TiN | 3 | 3 | 3 | 3 | 3 |
| TiC | 4 | 4 | 4 | 4 | 4 |

| CRITERION | | DETERMINATION RESULT |
|---|---|---|
| SOLID PHASE RATE $X_{cs}$ $(C_x/C_w)$ | RESIN DECOMPOSITION RATE $X_{rs}$ [wt%] | |
| $X_{cs} \leq 0.06$ | $X_{rs} = 0.00$ | 01 |
| $X_{cs} \leq 0.06$ | $X_{rs} > 0.00$ | 02 |
| $X_{cs} > 0.06$ | $X_{rs} = 0.00$ | 03 |
| $X_{cs} > 0.06$ | $X_{rs} > 0.00$ | 04 |

Dh
- 01 → SUPPORT MESSAGE mr
- 02 → SUPPORT MESSAGE m1
- 03 → SUPPORT MESSAGE m2
- 04 → SUPPORT MESSAGE m3

MOLDING SUPPORT DEVICE FOR INJECTION MOLDING MACHINE

TECHNICAL FIELD

The present invention relates to a molding support device for an injection molding machine that is preferably used to provide molding support to an injection molding machine that injects plasticized molten resin with a screw into a metal mold to fill the mold with the resin to perform a molding operation.

BACKGROUND ART

Generally, an injection molding machine performs a molding operation by injecting plasticized molten resin with a screw into a metal mold to fill the mold with the resin. Thus, whether the molten resin can be maintained to have an appropriate molten state is an important factor to secure a desirable molding quality. In particular, when the plasticization proceeds excessively, the resin decomposition rate increases, which leads to defects such as the degeneration (e.g., carbonization) of molten resin or the generation of unnecessary gas. Such defects have a close relation with the molten resin-related molding conditions and the retention time, for example. The plasticization proceeds excessively when molding conditions are inappropriate or the retention time is lengthened, causing a risk of an increase in the resin decomposition rate. Thus, a technique has been suggested to grasp the state of the molten resin in a heating cylinder so that the required countermeasure processing is provided.

Conventionally, this type of technique includes known ones such as the injection molding machine disclosed in Patent Publication 1 and the plasticization simulation device disclosed in Patent Publication 2. The injection molding machine disclosed in Patent Publication 1 has a purpose of more accurately detecting the retention time of the resin in the cylinder and then judging the operation timing more accurately so as to prevent the degeneration of the resin in the cylinder. Specifically, the conveyance path of the resin in the cylinder is divided to zones 0-N. After the temperature increase, the retention times T(0)-T(N) of the resin of the respective zones are set to 0. Whenever one second passes, whether or not the screw rotation number from the previous measurement is 1 or more is judged. When the screw rotation number from the previous measurement is 1 or less, 1 second is added to each of the retention times T(0)-T(N). When the screw rotation number from the previous measurement is 1 or more, the resin retention time is shifted in proportion with the number of the zones through which the resin is moved in accordance with the screw rotation number to use the retention times T(0)-T(N) of the respective zones. If there is no zone to be shifted, the retention time is set to 0. When resin is discharged by the injection, for example, the retention time T(N) of the zone at a tip end of the screw is set to 0 to calculate the retention times of the respective zones. When a resin retention prevention setting time Tmax is exceeded, alarm is issued and the temperature is lowered.

The plasticization simulation device disclosed in Patent Publication 2 is a plasticization simulation device to perform physical quantity calculation processing to use the resin property of the material used in a screw-type plasticization device, the operation conditions of the plasticization device, and configuration data of the plasticization device to use a screw characteristic formula, a mass conservation formula, and an energy preservation formula to calculate at least one physical quantity among the solid phase rate, the temperature, the pressure, and the plasticizing capacity. In particular, an analysis unit is provided that calculates the physical quantity in the screw rotation state by means of physical quantity calculation processing to use the calculated physical quantity to use the screw characteristic formula, the mass conservation formula, and the energy preservation formula to thereby calculate the physical quantity in the state where the screw is stopped.

PRIOR ART PUBLICATION

Patent Publication

Patent Literature 1: Japanese Unexamined Patent Application Publication No. 2005-022260
Patent Literature 2: Japanese Unexamined Patent Application Publication No. 2015-123668

DISCLOSURE OF THE INVENTION

Problem to be Solved by the Invention

However, the above-described conventional technique to grasp the molten resin state to perform a required countermeasure processing has a disadvantage as described below.

First, abnormal plasticization occurs not only when excessive plasticization is caused, but also when insufficient plasticization is caused. Specifically, when there is insufficient plasticization, insufficiently-plasticized molten resin causes the solid phase rate (un-melted polymer fraction) to increase, which causes defects such as a lower moldability and a lower molding quality. The above-described conventional technique is primarily merely a technique to avoid excessive plasticization and thus is not necessarily sufficient to widely grasp the molten state based on which an appropriate countermeasure processing is performed. Thus, desirable molding processing can be performed by setting and securing a suitable range to the molten state. However, the conventional technique is merely a "one-sided technique", based on only one side, thus leaving room for further improvement from the viewpoint of higher moldability and molding quality.

Secondly, whether or not the plasticization proceeds excessively can be grasped relatively easily by finding the retention time of the resin in the heating cylinder, for example. However, grasping the insufficiently-plasticized molten resin is not necessarily easy. Thus, there has been no conventional technique to appropriately (or quantitatively) grasp the molten state of the molten resin. The reality is generally that an operator visually observes a molded article to rely on a judgement of the state based on this. Thus, a new molding support device has been required that can appropriately (or quantitatively) find an insufficiently-plasticized molten resin to provide an appropriate countermeasure.

It is an objective of the present invention to provide a molding support device for an injection molding machine to solve the problem existing in the related technique.

Means for Solving the Problem

In order to solve the above-described disadvantage, the present invention provides a molding support device 1 for an injection molding machine that performs molding support for an injection molding machine M in which plasticized molten resin is injected with a screw 3 into a metal mold 2 to mold the resin. The molding support device 1 is characterized by comprising: a basic data input unit Fi that inputs basic data Do including molding conditions data Dm related to at least molding conditions and screw data Ds related to the form of the screw 3; a calculation formula data setting unit Fs that sets the solid phase rate calculation formula data Dc to calculate, based on this basic data Do, the solid phase rate Xc of the molten resin in the heating cylinder 4; a calculation processing function unit Fc that has a solid phase rate calculation processing unit Fcp to use calculation processing based on the basic data Do and the solid phase rate calculation formula data Dc to calculate an estimated solid phase rate Xcs of the molten resin at the measurement completion; and an output processing function unit Fd that performs display processing to display information related to the estimated solid phase rate Xcs on a display 5.

In this case, according to a preferred embodiment of the invention, the molding conditions data Dm can include data related to the type of resin material to be used. The screw data Ds can include data related to the type of the material of the screw surface 3f On the other hand, the calculation formula data setting unit Fs can set decomposition rate calculation formula data Dr to calculate, based on the basic data Do, the resin decomposition rate Xr of the screw surface 3f during a molding operation. The calculation processing function unit Fc can have a decomposition rate calculation processing unit Fcr to calculate an estimated resin decomposition rate Xrs by means of calculation processing based on the basic data Do and the decomposition rate calculation formula data Dr. A determination processing unit Fcj can be provided that performs determination processing to determine the level of the estimated solid phase rate Xcs and/or the estimated resin decomposition rate Xrs to output the support message data Dh corresponding to the result of the determination processing. On the other hand, the output processing function unit Fd can have a function to allow a message display unit 5d of the display 5 to display the support messages mr, m1, and m2 . . . based on the support message data Dh outputted from the determination processing unit Fcj. The support messages mr, m1, and m2 . . . can be allowed to include determination messages mrj, m1j, and m2j . . . showing the result of the determination processing and countermeasure messages m1p and m2p . . . to perform countermeasures in accordance with the determination messages m1j and m2j . . . . On the other hand, the calculation formula data setting unit Fs can set the temperature increase calculation formula data Dw to calculate an estimated temperature increase ΔT based on data related to shearing heating value E used for the calculation processing by means of the resin decomposition rate calculation formula data Dr. The calculation processing function unit Fc can have a temperature increase calculation processing unit Fct that calculates the estimated temperature increase ΔT by means of calculation processing based on the temperature increase calculation formula data Dw. The output processing function unit Fd can have a temperature increase display unit 10 to allow the display 5 to display the estimated temperature increase ΔT calculated by the temperature increase calculation processing unit Fct.

Effects of the Invention

Significant effects as shown below are provided by the molding support device 1 for the injection molding machine according to the present invention described above.

(1) The defect of the conventional method in which, in order to grasp the molten state of insufficiently-plasticized molten resin, for example, an operator visually observes a molded article to then rely on judgement of the state based on the visual observation, can be solved. In order to do this, the insufficiently-plasticized molten resin can be grasped appropriately (or quantitatively) so as to take an appropriate countermeasure. Specifically, personal judgement requiring experience, for example, is not required any more, allowing even a beginner operator having little experience to perform a more desirable molding (production) by increasing the yield rate and the molding quality of molded articles, for example.

(2) According to a preferred embodiment, molding conditions data Dm including data related to the type of resin material to be used allows the property of each resin material type (e.g., melting characteristic) to be reflected in the calculation of the estimated solid phase rate Xcs, thus providing a more appropriate (or accurate) estimated solid phase rate Xcs.

(3) According to a preferred embodiment, a more appropriate (or accurate) estimated resin decomposition rate Xrs can be provided because screw data Ds including data related to the type of material of the screw surface 3f allows the calculation of the estimated resin decomposition rate Xrs to be carried out while reflecting the catalyst effect by the metal material of the screw surface 3f on the molten resin and a degradation factor caused by how much the former is easily attached to the latter, thus providing a more appropriate (or accurate) estimated resin decomposition rate Xrs.

(4) According to a preferred embodiment, the calculation formula data setting unit Fs sets the decomposition rate calculation formula data Dr to calculate, based on the basic data Do, the resin decomposition rate Xr of the screw surface 3f during a molding operation. This can provide a simple calculation of the estimated resin decomposition rate Xrs because the basic data Do used for the calculation processing of the solid phase rate calculation formula data Dc also can be used for the calculation processing of the decomposition rate calculation formula data Dr.

(5) According to a preferred embodiment, the calculation processing function unit Fc has the decomposition rate calculation processing unit Fcr to calculate the estimated resin decomposition rate Xrs by means of the calculation processing based on the basic data Do and the decomposition rate calculation formula data Dr. This provides the estimated resin decomposition rate Xrs according to the calculation processing in an easy manner. Thus, based on the estimated resin decomposition rate Xrs, the deterioration state of the molten resin can be grasped appropriately. Thus, the suitable range of the molten state can be set based on both one side's (the insufficient plasticization-side) limit point of the molten state based on the estimated solid phase rate Xcs, and the other side's (the excessive plasticization-side) limit point of the molten state based on the estimated resin decomposition rate Xrs, thus providing higher moldability and molding quality.

(6) According to a preferred embodiment, the calculation processing function unit Fc has the determination processing unit Fcj that performs determination processing on the level of the estimated solid phase rate Xcs and/or the estimated resin decomposition rate Xrs to output the support message data Dh corresponding to the result of the determination processing. The output processing function unit Fd has a function to allow the message display unit 5d of the display 5 to display the support messages mr, m1, and m2 . . . based on the support message data Dh output from the determination processing unit Fcj. The operator can use visual means to easily grasp the molten state of molten resin that is difficult to judge and can promptly perform the required countermeasure processing.

(7) According to a preferred embodiment, the support messages mr, m1, and m2 . . . include the countermeasure messages m1p and m2p . . . that provide countermeasures in accordance with determination messages mrj, m1j, and m2j . . . showing the result of the determination processing and the determination messages m1j and m2j . . . . This allows even a beginner operator having little experience, to easily and securely confirm whether or not the molten state of the molten resin is suitable, and to promptly take the required countermeasure (e.g., a change of the setting of the molding conditions), thus providing the efficient and streamlined production of molded articles.

(8) According to a preferred embodiment, the calculation formula data setting unit Fs sets the temperature increase calculation formula data Dw that calculates the estimated temperature increase $\Delta T$ based on data related to the shearing heating value E used for the calculation processing by the resin decomposition rate calculation formula data Dr. As a result, the data related to the shearing heating value E used for the calculation processing by the resin decomposition rate calculation formula data Dr can also be used for the calculation processing of the temperature increase calculation formula data Dw, thus allowing the estimated temperature increase $\Delta T$ to be easily calculated.

(9) According to a preferred embodiment, the calculation processing function unit Fc includes the temperature increase calculation processing unit Fct that calculates the estimated temperature increase $\Delta T$ by calculation processing based on the temperature increase calculation formula data Dw. The output processing function unit Fd includes the temperature increase display unit 10 that allows the display 5 to display the estimated temperature increase $\Delta T$ calculated by the temperature increase calculation processing unit Fct. This consequently provides the collective visual confirmation of information related to the estimated solid phase rate Xcs and/or the estimated resin decomposition rate Xrs as well as information related to the estimated temperature increase $\Delta T$, thus allowing understanding of the resin molten state in a more-appropriate manner.

DESCRIPTION OF REFERENCE NUMERALS

1: Molding support device, 2: Metal mold, 3: Screw, 3f: Screw surface, 4: Heating cylinder, 5: Display, 5d: Message display unit, 10: Temperature increase display unit, M: Injection molding machine, Do: Basic data, Dm: Molding conditions data, Ds: Screw data, Dc: Solid phase rate calculation formula data, Dr: Decomposition rate calculation formula data, Dw: Temperature increase calculation formula data, Dh: Support message data, Fi: Basic data input unit, Fs: Calculation formula data setting unit, Fc: Calculation processing function unit, Fcp: Solid phase rate calculation processing unit, Fcr: Decomposition rate calculation processing unit, Fcj: Determination processing unit, Fct: Temperature increase calculation processing unit, Fd: Output processing function unit, Xc: Solid phase rate, Xcs: Estimated solid phase rate, Xr: Resin decomposition rate, Xrs: Estimated resin decomposition rate, mr: Support message, m1: Support message, m2 . . . : Support message, mrj: Determination message, m1j: Determination message, m2j . . . : Determination message, m1p . . . : Countermeasure message, m2p . . . : Countermeasure message, E: Shearing heating value-related data, $\Delta T$: Estimated temperature increase

BEST MODE FOR CARRYING OUT THE INVENTION

Next, the following section will describe the best embodiment of the present invention in detail based on the drawings.

Figure 1:
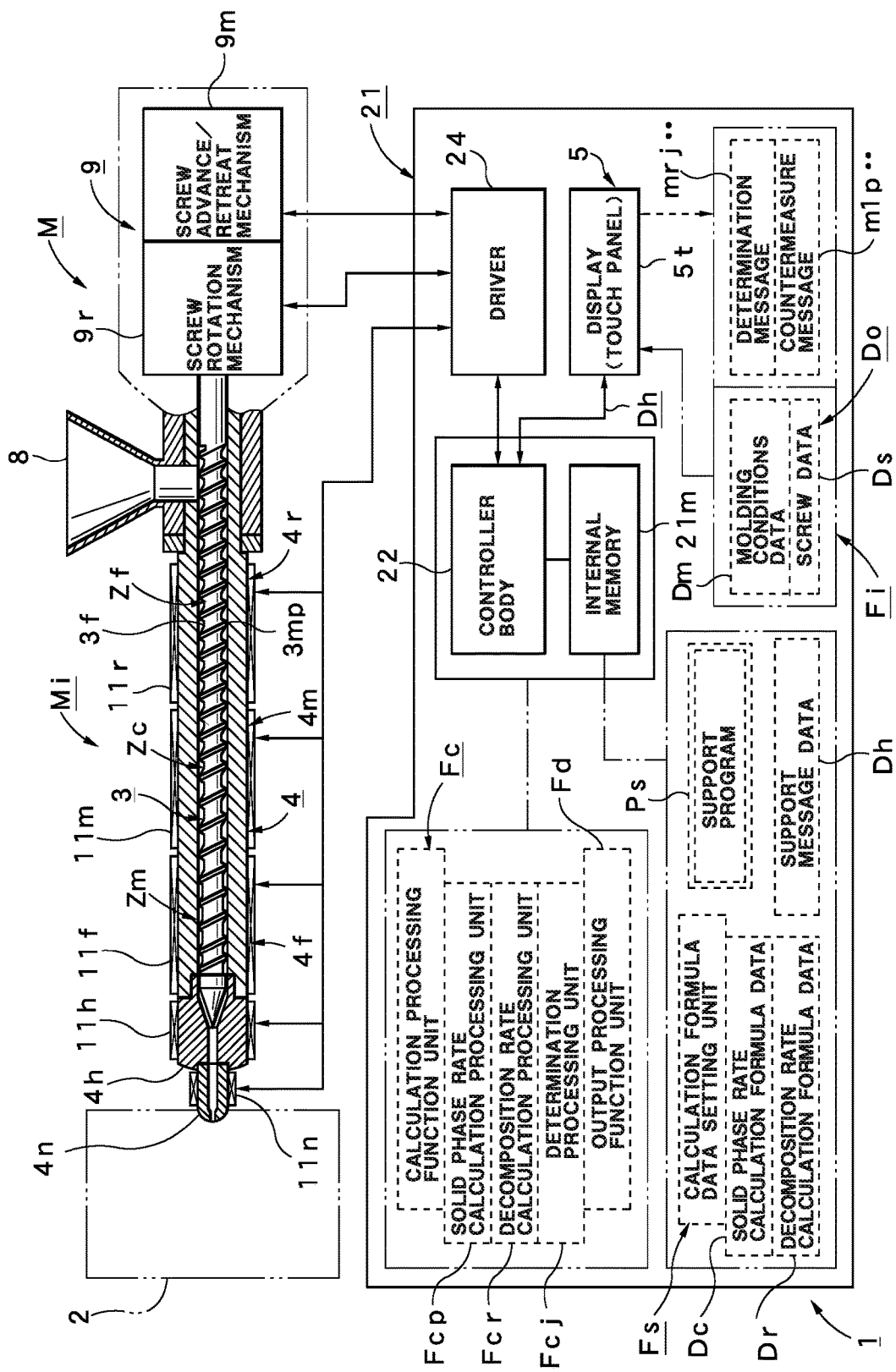
FIG. 1 is a block system diagram illustrating an injection molding machine including a molding support device according to the best embodiment of the present invention.

First, in order to provide an easy understanding of the molding support device 1 according to this embodiment, the following section will describe the outline of the injection molding machine M that can use the molding support device 1 with reference to FIG. 1.

FIG. 1 illustrates the injection molding machine M and in particular, the injection device Mi, in which a clamping device is omitted. In the injection device Mi, the reference numeral 4 denotes a heating cylinder. This heating cylinder 4 has, at the front end thereof, a nozzle 4n fixedly attached via a head unit 4h. The heating cylinder 4 has a hopper 8 at the upper side of the rear end thereof. The nozzle 4n has a function to inject the molten resin in the heating cylinder 4 to the metal mold 2 shown by the phantom line. The hopper 8 has a function to supply resin material (resin pellet) to the interior of the heating cylinder 4.

The interior of the heating cylinder 4 includes therein the screw 3 that is attached in a freely rotatable and retractable manner. The surface of the screw 3 has thereon a helical flight unit 3mp. A screw surface 3f is subjected to coating processing by a predetermined surface material (metal) in consideration of durability, for example. This screw 3 has a metering zone Zm, a compression zone Zc, and a feed zone Zf in an order from the front side to the rear side. On the other hand, the rear end of the screw 3 is coupled to a screw driving unit 9. The screw driving unit 9 includes a screw rotation mechanism 9r to rotate the screw 3 and a screw advance/retreat mechanism 9m to move the screw 3 forward and rearward. The screw rotation mechanism 9r and the screw advance/retreat mechanism 9m may be driven by any driving method such as a hydraulic method using a hydraulic circuit or an electrical method using an electric motor.

The heating cylinder 4 has, in an order from the front side to the rear side, a heating cylinder front part 4f, a heating cylinder middle part 4m, and a heating cylinder rear part 4r. The respective parts 4f, 4m, and 4r have, on the outer circumferential face thereof, a front part heating unit 11f, a middle part heating unit 11m, and a rear part heating unit 11r, respectively. Similarly, the head unit 4h has, on the outer circumferential face thereof, a head heating unit 11h. The nozzle 4n has, on the outer circumferential face thereof, a nozzle heating unit 11n. The respective heating units 11f, 11m, 11r, 11h, and 11n can be configured by a band heater, for example.

On the other hand, the reference numeral 21 denotes a molding machine controller performing overall control of the injection molding machine M. The molding machine controller 21 includes a controller body 22 having computer functions, including hardware such as CPU and an accompanying internal memory 21m. The connection port of the controller body 22 is connected to the display 5 accompanying the controller body 22 and is connected to a driver 24 to drive (operate) various actuators. In this case, the display 5 can perform a required information display and includes a touch panel 5t. This touch panel 5t can be used to provide various operations such as input, setting, or selection operations. The driver 24 is connected to the screw rotation mechanism 9r and the screw advance/retreat mechanism 9m described above and is connected to the respective heating units 11f, 11m, 11r, 11h, and 11n. This allows the controller body 22 to control, via the driver 24, the driving of the screw rotation mechanism 9r and the screw advance/retreat mechanism 9m and to control the energization of the respective heating units 11f, 11m, 11r, 11h, and 11n.

Thus, the molding machine controller 21 includes an HMI (human-machine interface) control system and a PLC (programmable logic controller) control system. An internal memory 21m stores therein the PLC program and the HMI program. The PLC program is software to realize the monitoring of the sequence operation of various steps in the injection molding machine M and the injection molding machine M, for example. The HMI program is software to realize the setting and display of the operation parameters of the injection molding machine M and the display of the operation monitoring data of the injection molding machine M, for example.

Next, the following section will describe the configuration of the molding support device 1 according to this embodiment that can be used for such an injection molding machine M with reference to FIG. 1-FIG. 7 and FIG. 8a-FIG. 8d.

The molding support device 1 according to this embodiment is configured to include the controller body 22 and the display 5 constituting the above-described molding machine controller 21. Thus, the internal memory 21m of the controller body 22 stores therein a support program Ps by means of an application program to allow the molding support device 1 to function.

As shown in FIG. 1, the molding support device 1 includes the basic data input unit Fi to input the basic data Do including the molding conditions data Dm related to at least molding conditions and the screw data Ds related to the form of the screw 3. This basic data input unit Fi ca use the touch panel 5t provided on the display 5. In this case, the display 5 displays an input screen (not shown). Thus, a required value can be inputted or selected, for example, through the touch panel St. The display 5 displays a message display unit 5d (which will be described later). This message display unit 5d displays support messages mr, m1, m2, and m3.

The molding conditions data Dm includes various pieces of data related to molding conditions for the molding operation by the injection molding machine M (specifically, basic data related to various physical quantities such as a melt flow rate, a screw rotation number, a measuring time, a backpressure, a measuring position, a front part temperature, a middle part temperature, a rear part 1 temperature, a rear part 2 temperature, or a cycle time) and a plurality of pieces of data related to the molding conditions (e.g., data related to the type of resin material to be used). Data related to the resin material types includes the various properties of each resin material (e.g., melting characteristics). As described above, the molding conditions data Dm including data related to the type of resin material to be used allows the calculation of the estimated solid phase rate Xcs (which will be described later) to reflect the property of each resin material type (e.g., melting characteristics), thus providing more appropriate (or accurate) estimated solid phase rate Xcs.

The screw data Ds includes various pieces of data related to the form of the screw 3 (specifically, a screw outer diameter, a screw flight width, a friction coefficient between a piece of solid matter and a screw, a screw groove depth, a screw width direction length, a screw lead, a flight coefficient and a screw flight torsion angle), data related to various dimensions (e.g., a pitch number), and a plurality of various pieces of data related to screws (data related to the type of material of the screw surface 3f, for example). By means of the screw data Ds including data related to the type of material of the screw surface 3f, the calculation of the estimated resin decomposition rate Xrs can include a reflection of the catalyst effect by the metal material of the screw surface 3f on the molten resin and the degradation factor caused by how easily the former is attached to the latter, thus providing a more appropriate (or accurate) estimated resin decomposition rate Xrs.

The molding support device 1 includes the calculation formula data setting unit Fs using the internal memory 21m. This calculation formula data setting unit Fs sets the solid phase rate calculation formula data Dc and the decomposition rate calculation formula data Dr. The solid phase rate calculation formula data Dc is data related to a calculation formula to calculate the solid phase rate Xc of the molten resin in the heating cylinder 4 based on the above-described basic data Do. The decomposition rate calculation formula data Dr is data related to a calculation formula to calculate the resin decomposition rate Xr of the screw surface 3f during a molding operation based on the above-described basic data Do. As described above, by setting the solid phase rate calculation formula data Dc and the decomposition rate calculation formula data Dr, the estimated resin decomposition rate Xrs can be simply calculated because the basic data Do used for the calculation processing of the solid phase rate calculation formula data Dc can also be used for the calculation processing of the decomposition rate calculation formula data Dr, for example.

Next, the following section will describe a solid phase rate calculation formula to calculate the solid phase rate Xc which is the foundation of the solid phase rate calculation formula data Dc.

Figure 2:
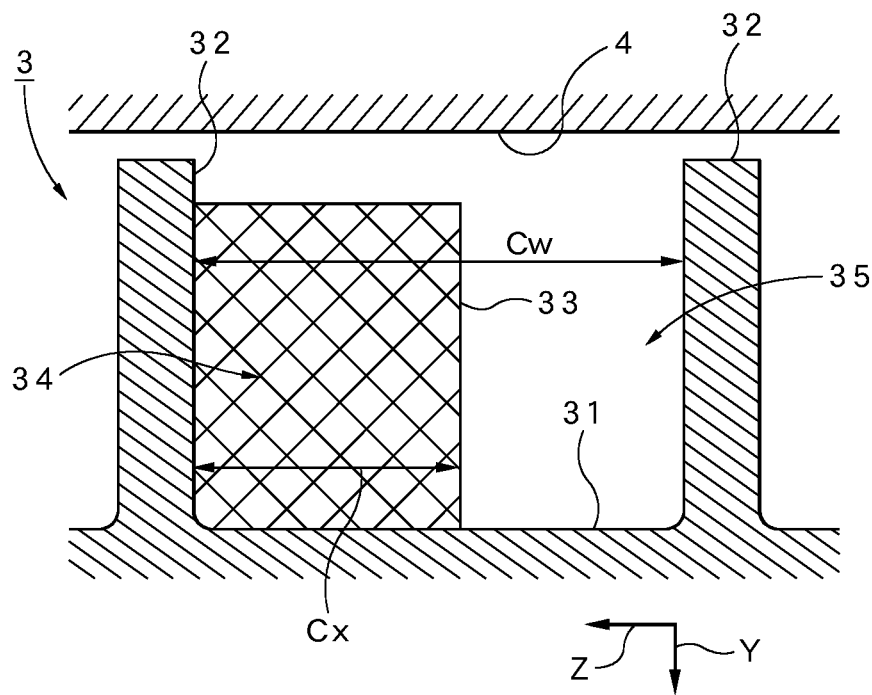
FIG. 2 illustrates the principle of a screw to explain the calculation function of a solid phase rate calculation processing unit included in the molding support device.

FIG. 2 illustrates the principle of the screw 3 to explain the calculation function of the solid phase rate Xc. In FIG. 2, the reference numeral 3 denotes a screw, the reference numeral 4 denotes a heating cylinder, the reference numeral 31 denotes a screw groove bottom, the reference numeral 32 denotes a screw flight, the reference numeral 33 denotes a melt film, the reference numeral 34 denotes a solid bed, and the reference numeral 35 denotes a melt pool, respectively. The reference numeral Cx denotes the width of a piece of solid matter at the current position and the reference numeral Cw denotes a length obtained by deducting the flight width from the pitch width, respectively.

One example of the solid phase rate calculation formula used in this embodiment is shown in [formula 101].

$$\text{Solid phase rate } Xc = Cx/Cw \qquad \text{[formula 101]}$$
$$= (Cx'/Cw) \cdot (1 - ka - \Phi i)$$
$$\text{wherein } \Phi i = f(Tr, Tc) \cdot \Phi e.$$

As shown in [formula 101], the solid phase rate Xc can basically be calculated based on Cx/Cw. In [formula 101], the reference numeral Cx' denotes the width of the piece of solid matter one pitch earlier, the reference numeral ka denotes an adjustment coefficient, the reference numeral $\Phi i$ denotes a melting rate during an injection operation, the reference numeral $\Phi e$ denotes a melting rate during an extrusion operation, the reference numeral Tr denotes the measuring time, and the reference numeral Tc denotes a cycle time, respectively.

Generally, with regard to a melting mechanism including a continuously-operating heating cylinder as in an extrusion molding machine, a known formula suggested by Tadmor in 1978 has been widely used as a theory formula to predict a plasticization state.

On the other hand, the injection molding machine M performs an intermittent operation (injection→measurement→standby). Thus, the injection molding machine M includes injection conditions different from those of the extrusion molding machine (e.g., a different injection position and screw stoppage time). Thus, a known model formula cannot be directly applied to the injection molding machine M. Thus, the solid phase rate calculation formula used in this embodiment converts a model formula applicable to an extrusion molding machine to a model formula applicable to the injection molding machine M (specifically, with regards to a model formula applicable to the extrusion molding machine, the solid phase rate calculation formula uses $\Phi i$ obtained by multiplying a function formula including a measuring time Tr and a cycle time Tc (e.g., f (Tr,Tc)·$\Phi e$ shown in [formula 101]), with the rate $\Phi e$ at which resin material is molten (which is an amount suggesting the melting rate and which has a dimensionless unit).

By using the calculation formula shown in [formula 101] as described above, the model formula applicable to the extrusion molding machine is converted to the model formula applicable to the injection molding machine M, thus providing the calculation of the solid phase rate Xc showing the melting ratio (melting level) of the molten resin in the heating cylinder 4 in which the screw 3 is stored. Thus, the solid phase rate Xc obtained by this solid phase rate calculation formula can be used as the estimated solid phase rate Xc obtained based on the inputted basic data Do (i.e., the estimated solid phase rate Xcs).

Furthermore, this estimated solid phase rate Xcs is examined with regard to whether or not the estimated solid phase rate Xcs matches the solid phase rate obtained by actually measuring actually-obtained molten resin. After an adjustment is performed, a substantially matching solid phase rate calculation formula is set as the solid phase rate calculation formula data Dc in this embodiment.

In [formula 101], the closer the term (1−ka·$\Phi i$) is to 0 (i.e., the higher the rate $\Phi i$), the closer the solid phase rate Xc is to 0, suggesting that the molten resin in the heating cylinder 4 is completely molten. In the embodiment, how much un-melted solid matter is left is calculated based on the solid phase rate Xc to consider the correlation with the change of the resin temperature during the molding operation. The thickness of the melt film 33 is generally used to calculate the shear heating. However, there is a significant difference between the actual measurement value and the calculation value. To solve this, in this embodiment, the solid phase rate in the fully-melted state (adjustment value) is specified and a solid phase and a liquid phase are separately used and the calculation is performed based on an assumption that the shear heating is caused only in the liquid phase. The result showed substantial matching with the actual measurement value.

Figure 3:
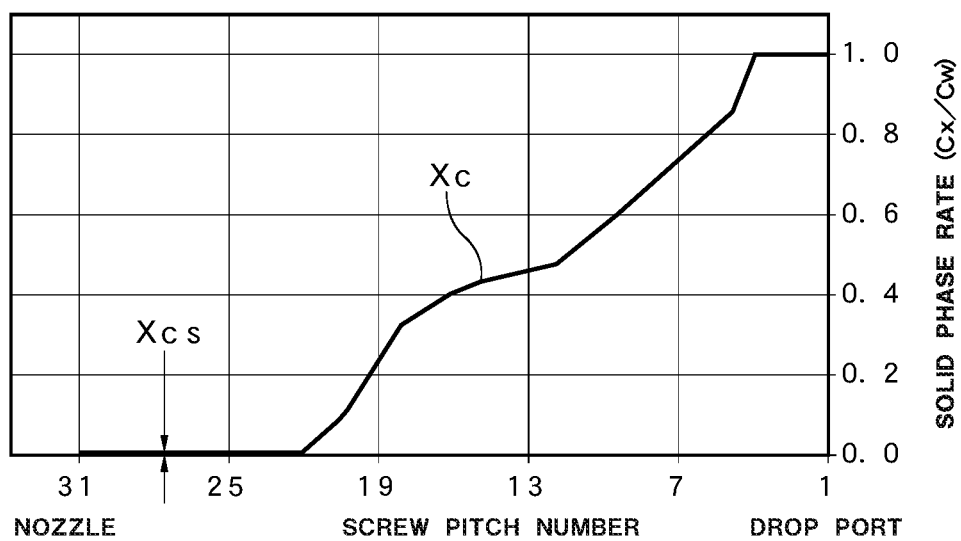
FIG. 3 illustrates the characteristic of a change in the solid phase rate relative to the screw position in order to explain the calculation function of the solid phase rate calculation processing unit included in the molding support device.

FIG. 3 illustrates a change of the solid phase rate Xc relative to the position of the screw 3 obtained from the solid phase rate calculation formula. In FIG. 3, the horizontal axis shows a screw pitch number, and the higher the number the shorter the distance to the nozzle side. The vertical axis shows the solid phase rate Xc, and the closer the solid phase rate Xc to 0, the closer to a completely-molten state. The solid phase rate Xc 0 shows a completely-molten state. In FIG. 3, the solid phase rate Xc at the position shown by Xcs is assumed to be the estimated solid phase rate Xcs of the molten resin at the measurement completion.

The estimated solid phase rate Xcs does not have to be 0 from a practical viewpoint. This criterion is desirably selected as "0.06". This value was confirmed based on the experiment result. This can lead, when the estimated solid phase rate Xcs is "Xcs≤0.06", to the judgement that the molten state is in a preferred state and, when "Xcs>0.06" is established, to the judgement that the melting is insufficient (insufficient plasticization). In this manner, the magnitude of the estimated solid phase rate Xcs functions as an indicator showing the molten state of the insufficiently-plasticized molten resin, for example. The estimated solid phase rate Xcs shows the melting level of the molten resin. Thus, an un-melted polymer fraction may be used.

Next, the following section will describe the decomposition rate calculation formula to calculate the resin decomposition rate Xr which is a foundation of the decomposition rate calculation formula data Dr.

One example of the decomposition rate calculation formula used in this embodiment is shown in [formula 102].

Resin decomposition rate $Xr = E \cdot Wa \cdot kb$      [formula 102]

However, $E = f(W, L, \sigma, \gamma, \zeta)$ $Wa \propto f(\Phi m, \Phi c, Qs)$

[Formula 102] is basically based on the model formula of Tadmor and is a calculation formula to calculate the resin decomposition rate Xr in the injection molding machine M. In [formula 102], the reference numeral E denotes a shearing heating value [MJ] calculated based on the Tadmor model formula that is a total shear heating value obtained by integrating the shearing heating values in a range from a fully-melted position to a tip end of the screw 3. The reference numeral Wa denotes the adhesion work [MJ/m²] of the molten resin and metal, and the reference numeral kb shows an adjustment coefficient in consideration of the catalyst effect of the metal, respectively.

Figures 4, 5:
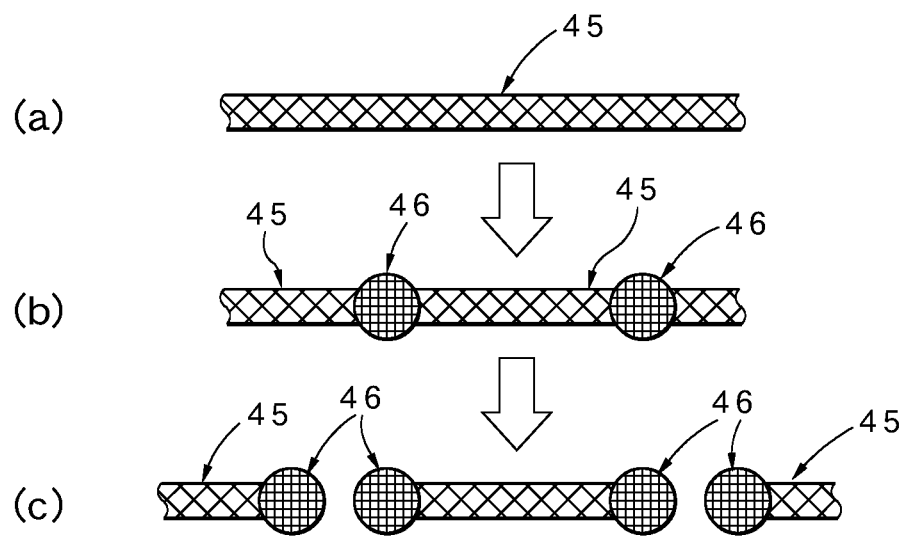
FIG. 4 illustrates the resin deterioration principle that is the foundation of the resin decomposition rate calculated by the resin decomposition rate calculation processing unit included in the molding support device.
FIG. 5 is a list showing how easily resin is adhered to metal which is the foundation of the resin decomposition rate.

In the calculation of the shearing heating value E, the reference numeral W denotes the length obtained by deducting a flight width from a pitch width, the reference numeral L denotes a screw spiral length, the reference numeral σ denotes a shearing stress, the reference numeral γ denotes a shearing rate, and the reference numeral denotes a dimensionless depth, respectively. In the calculation of the adhesion work Wa, the reference numeral Φm denotes the work function of the base material metal, the reference numeral Φc denotes the work function of metal coated on the base material metal, and the reference numeral Qs denotes the oxygen content attached to the outermost surface metal, respectively. The oxygen content Qs can be measured by an X-ray analysis device (EDX device). This adhesion work Wa shows how easily the molten resin can be adhered to metal. FIG. 5 shows how easily the molten resin can be adhered to the metal of the screw surface 3f for the respective types.

Figures 6, 7:
FIG. 6 is a list showing how easily resin is adhered to metal which is the foundation of the resin decomposition rate.
FIG. 7 illustrates the function of a determination processing unit provided in the molding support device.

The metal catalyst effect (oxidation induction time) functions as a degradation factor in regard to the molten resin. Thus, this catalyst effect is reflected in the coefficient kb. It is known that generally, when polymer (resin) is heated, hydrogen is extracted to cause a polymer radical active species. In the case of the polymer radical active species, this state does not cause a reduced molecular weight of the polymer. However, contact with metal causes a catalyst action to bring about a radical coupling with oxygen in the air, leading to a phenomenon of promoting the decomposition of molten resin. FIGS. 4(a)-4(c) are a schematic view of this phenomenon. FIG. 4(a) shows a state in which heat causes the activation (thermal decomposition) of a high polymer (polymer) 45. When a metal species causes catalyst activation in this state, an oxidization phenomenon as shown in FIG. 4(b) is caused, in which the activated polymer 45 is coupled to oxygen 46. When the oxidization further proceeds, as shown in FIG. 4(c), a low-molecularization phenomenon occurs due to the oxidization decomposition of the polymer 45. FIG. 6 shows, according to type, how easily molten resin is decomposed relative to the metal of the screw surface 3f.

The calculation result of the resin decomposition rate Xr based on decomposition rate calculation formula of [formula 102] considers the retention time of molten resin, an adhesion work, an oxidation induction time, and a screw shape, for example. Thus, the resin decomposition rate Xr obtained by the decomposition rate calculation formula can be used as the estimated resin decomposition rate Xr obtained based on the inputted basic data Do (i.e., the estimated resin decomposition rate Xrs). By setting such a decomposition rate calculation formula data Dr, the estimated resin decomposition rate Xrs can be simply calculated by using the above-described basic data Do used for the calculation processing of the solid phase rate calculation formula data Dc for the calculation processing of the decomposition rate calculation formula data Dr, for example.

It was confirmed that the experiment (demonstration) result showed no deterioration so long as the estimated resin decomposition rate Xrs of 0.00 was maintained. Thus, it is understood that when the estimated resin decomposition rate Xrs has a value higher than 0.00, the molten resin is in a deterioration state (including a case of a high risk of shift to the deterioration state). Specifically, when "Xrs=0.00" is established for the estimated resin decomposition rate Xrs, it can be judged that a preferred molten state is obtained without deterioration. When "Xrs>0.00" is established for the estimated resin decomposition rate Xrs, it can be judged that the deterioration state or a high risk of a shift to the deterioration state has been caused. As described above, the magnitude of the estimated resin decomposition rate Xrs can be used as an indicator showing the deterioration state of the molten resin caused by excessive plasticization.

On the other hand, the molding support device 1 includes the calculation processing function unit Fc shown in FIG. 1 to perform calculation processing using the above-described solid phase rate calculation formula data Dc and the decomposition rate calculation formula data Dr.

This calculation processing function unit Fc includes the solid phase rate calculation processing unit Fcp that uses calculation processing based on the basic data Do and the solid phase rate calculation formula data Dc to calculate the solid phase rate Xc of the molten resin at the measurement completion (i.e., the estimated solid phase rate Xcs); and the decomposition rate calculation processing unit Fcr that uses calculation processing based on the basic data Do and the decomposition rate calculation formula data Dr to calculate the resin decomposition rate Xr of molten resin (i.e., the estimated resin decomposition rate Xrs).

As described above, the combination of the solid phase rate calculation processing unit Fcp and the decomposition rate calculation processing unit Fcr can easily provide the estimated resin decomposition rate Xrs by means of the calculation processing. Thus, the resultant estimated resin decomposition rate Xrs can provide an appropriate understanding of the deterioration state of the molten resin. Thus, the suitable range of the molten state can be set based on both one side's (the insufficient plasticization-side) limit point of the molten state based on the estimated solid phase rate Xcs and the other side's (the excessive plasticization-side) limit point of the molten state based on the estimated resin decomposition rate Xrs, thus providing higher moldability and molding quality.

The calculation processing function unit Fc includes the determination processing unit Fcj that performs determination processing on the level of the estimated solid phase rate Xcs and/or the estimated resin decomposition rate Xrs to output the support message data Dh corresponding to the result of the determination processing.

FIG. 7 shows the criteria for the determination processing. In FIG. 7, the determination result "01" shows a case where "Xcs≤0.06" and "Xrs=0.00" are both established. In this case, a sufficient molten state is obtained, and no deterioration state is found. Thus, a preferred molding environment can be judged. The determination result "02" shows a case where "Xcs≤0.06" and "Xrs>0.00" are both established. In this case, it can be judged that a sufficient molten state is obtained but there is a possibility of a deterioration state. The determination result "03" shows a case where "Xcs>0.06" and "Xrs=0.00" are both established. In this case, it can be judged that a possibility of an insufficient plasticization is caused, and no deterioration state is caused. The determination result "04" shows a case where "Xcs>0.06" and "Xrs>0.00" are both established. In this case, it can be determined that a possibility of an insufficient plasticization is caused, and a possibility of a deterioration state is caused.

The determination processing unit Fcj has a function to output the support message data Dh corresponding to the determination results "01"-"04". Specifically, a support message mr is outputted in the case of the determination result "0", a support message m1 is outputted in the case of the determination result "02", a support message m2 is outputted in the case of the determination result "03", and a support message m3 is outputted in the case of the determination result "04".

As shown in FIG. 1, the molding support device 1 includes the output processing function unit Fd. This output processing function unit Fd is a processing function to use the output of the determination result. In this embodiment, a display function is illustrated to allow the display 5 to display the above-described the support messages mr, m1, and m2 . . . . Although not shown, there may be other processing functions using the determination result, such as the one for an automatic correction processing to use data related to the estimated solid phase rate Xcs and data related to the estimated resin decomposition rate Xrs as correction data corresponding to the countermeasure messages m1p and m2p . . . to automatically correct the corresponding molding conditions.

The display function provided in the output processing function unit Fd shown in this embodiment can include two display functions.

The first display function as a base can have a display processing function to allow the display 5 to display the information related to the estimated solid phase rate Xcs. As described above, the estimated solid phase rate Xcs is an indicator showing the molten state of the molten resin. Thus, although not shown, it is possible to provide the numerical display of the solid phase rate Xc and the graphic display of the solid phase rate Xc by a bar graph, for example.

This can consequently solve the defect of the conventional method wherein the molten state of the insufficiently-plasticized molten resin, for example, requires an operator to visually observe a molded article, based on which the state is judged. Thus, the insufficiently-plasticized molten resin can be appropriately (or quantitatively) grasped to take an appropriate countermeasure. Specifically, personal judgement requiring experience, for example, is not required any more, to allow even a beginner operator having little experience to perform a more desirable molding (production) by increasing the yield rate and the molding quality of molded articles, for example.

In this case, the information related to the estimated solid phase rate Xcs is desirably displayed together with information related to the estimated resin decomposition rate Xr as an indicator showing the deterioration state of the molten resin. In this case, it is similarly possible to provide the numerical display of the estimated resin decomposition rate Xrs and the magnitude of the estimated resin decomposition rate Xrs by means of a bar graph for example.

The second display function is a function to allow the message display unit 5d of the display 5 to display the above-described support messages mr, m1, m2, and m3 based on the support message data Dh outputted from the determination processing unit Fcj.

The support messages mr, m1, m2, and m3 are allowed to include the determination messages mrj, m1j, m2j, and m3j showing the result of the determination processing as well as countermeasure messages m1p, m2p, and m3p to perform a countermeasure in accordance with the determination messages m1j, m2j, and m3j. Thus, the internal memory 21m stores therein support message data Dh corresponding to the support messages mr, m1, m2, and m3.

FIG. 8a-FIG. 8d illustrate one example of the support messages mr, m1, and m2 . . . in the message display unit 5d. In the illustrated case, the upper column displays the determination messages m1j and m2j . . . showing the result of the determination processing as required while the lower column displays the countermeasure messages m1p and m2p . . . to perform a countermeasure in accordance with the determination messages m1j and m2j . . . .

Figure 8A:
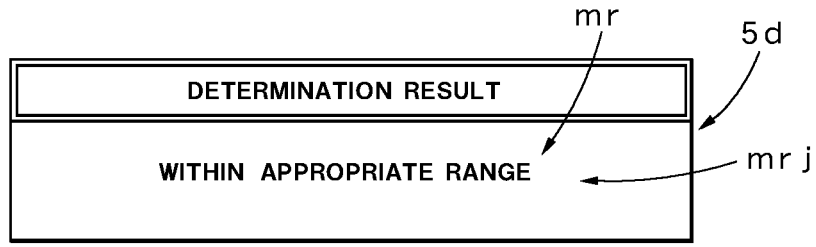
FIG. 8a illustrates a display screen showing one example of a determination message displayed by an output processing function unit provided in the molding support device.
Figure 8B:
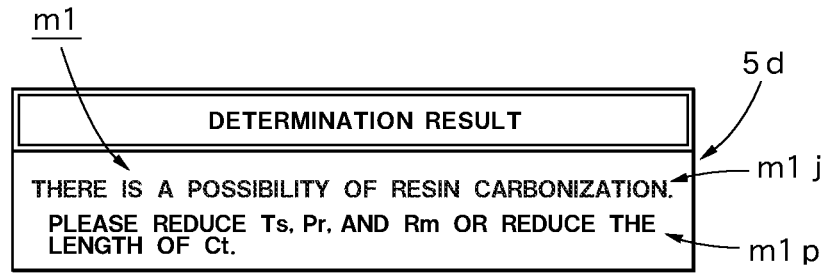
FIG. 8b illustrates another display screen showing one example of the determination message displayed by the output processing function unit provided in the molding support device.
Figure 8C:
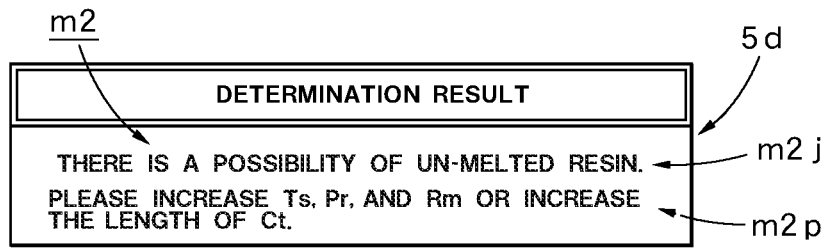
FIG. 8c illustrates another display screen showing one example of the determination message displayed by the output processing function unit provided in the molding support device.
Figure 8D:
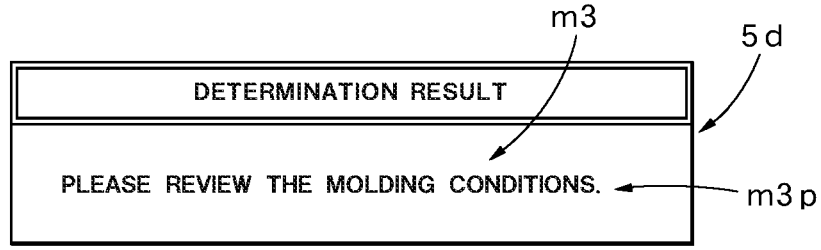
FIG. 8d illustrates another display screen showing one example of the determination message displayed by the output processing function unit provided in the molding support device.

Specifically, in the case of the support message mr, as shown in FIG. 8a, a determination message mrj is displayed that shows the characters: "Within the suitable range". In the illustrated case, no countermeasure message is displayed. However, a required countermeasure message may be displayed even when the suitable range is achieved (i.e., a message for providing further improvement by means of a change), for example. In the case of the support message m1, the determination message m1j as shown in FIG. 8b is displayed to show the characters: "There is a possibility of resin carbonization", for example. The countermeasure message m1p is displayed to show the characters: "Please reduce Ts, Pr, and Rm or reduce the length of Ct" (Ts: set temperature for a heating operation, Pr: backpressure, Rm: rotation number, Ct: cycle time), for example. Similarly, in the case of the support message m2, the determination message m2j as shown in FIG. 8c is displayed to show the characters: "There is a possibility of un-melted resin", for example, and the countermeasure message m2p is displayed to show the characters: "Please increase Ts, Pr, and Rm or increase the length of Ct", for example. In the case of the support message m3, the countermeasure message m3p as shown in FIG. 8d is displayed to show the characters: "Please review the molding conditions", for example, to prompt user to entirely reset the molding conditions. In the illustrated case, determination messages are not individually displayed and are substantially included in the countermeasure message m3p.

As described above, the calculation processing function unit Fc includes the determination processing unit Fcj to perform determination processing to determine the level of the estimated solid phase rate Xcs and/or the estimated resin decomposition rate Xrs to output the support message data Dh corresponding to the result of the determination processing. The output processing function unit Fd has a function to allow the message display unit 5d of the display 5 to display the support messages mr, m1, and m2 . . . based on the support message data Dh outputted from the determination processing unit Fcj. This allows an operator to use visual means to easily find the molten state of the molten resin that is difficult to judge and to carry out the required countermeasure processing promptly.

In particular, the support messages mr, m1, and m2 . . . are allowed to include the determination messages mrj, m1j, and m2j . . . showing the result of the determination processing and the countermeasure messages m1p and m2p . . . to perform a countermeasure in accordance with the determination messages m1j and m2j . . . . This allows even a beginner operator having little experience, to easily and securely confirm whether or not the molten state of the molten resin is suitable and to promptly take a required countermeasure (e.g., a change of the setting of the molding conditions), thus providing the efficient and streamlined production of molded articles.

Figure 9:
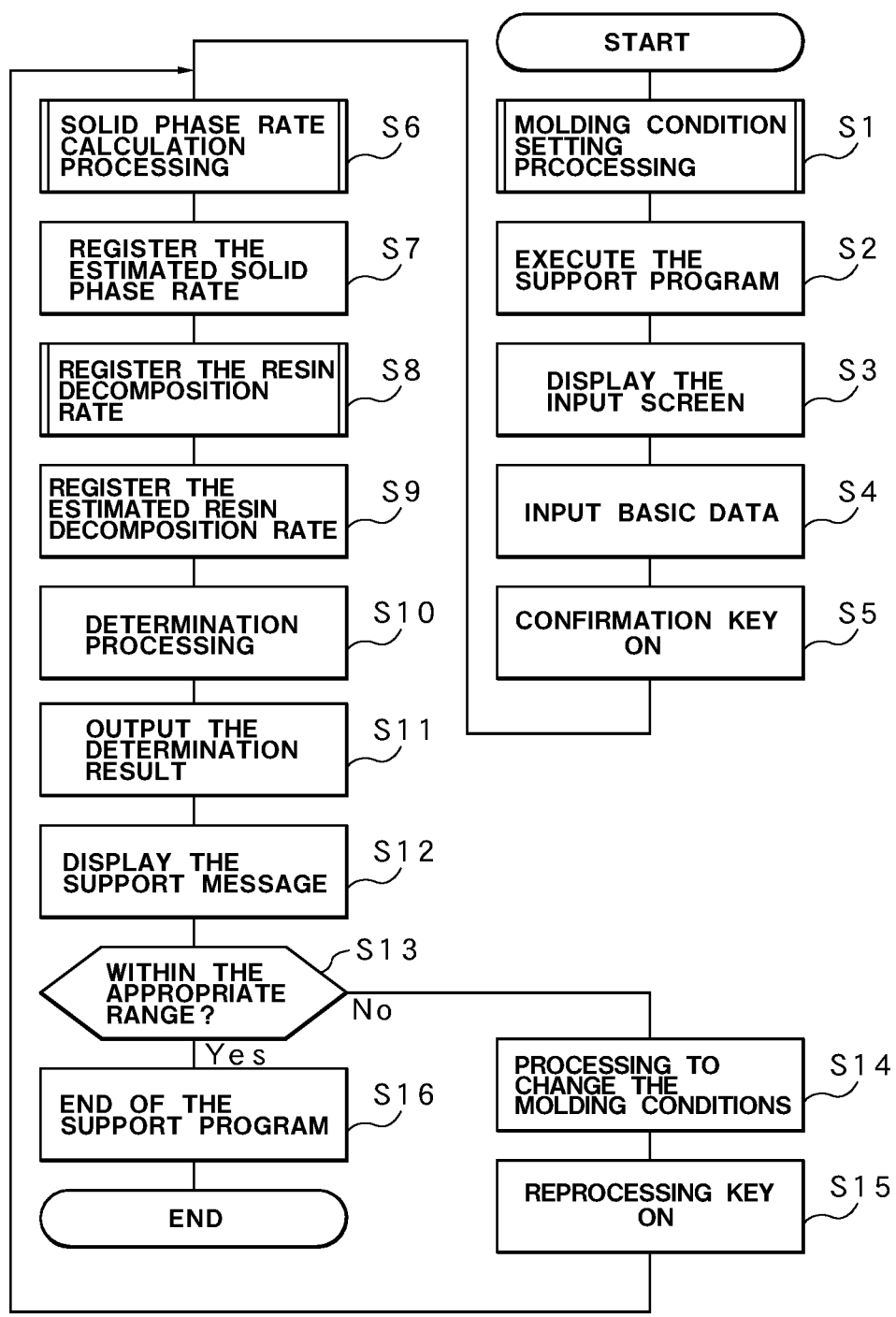
FIG. 9 is a flowchart illustrating a processing procedure of the molding support method of the injection molding machine according to the best embodiment of the present invention.

Next, the following section will describe a molding support method using the molding support device 1 according to this embodiment with reference to the respective drawings and with reference to the flowchart shown in FIG. 9.

The molding support device 1 can be basically used to set the molding conditions prior to the start of the production. This molding support method is carried out by the support program Ps stored in the internal memory 21*m*.

First, the operator performs, based on a general setting procedure, setting processing to set the molding conditions in the injection molding machine M (Step S1). In this case, the setting processing to set the molding conditions is performed by setting the information related to general molding conditions (i.e., general various pieces of information (conditions) to operate the injection molding machine M).

In order to use the molding support device 1 according to this embodiment after the completion of the setting processing of the molding conditions, a predetermined support start key (not shown) is turned ON to activate the molding support device 1 to thereby execute the support program Ps (Step S2). As a result, the display 5 displays an input screen (not shown) (Step S3).

Then, the touch panel 5*t* (the basic data input unit Fi) corresponding to displayed input screen is used to input the above-described basic data Do including the molding conditions data Dm related to the molding conditions set in advance and the screw data Ds related to the form of the screw 3 (Step S4). Specifically, this input can be performed by directly inputting a value or by selecting an input through a window display. In this case, no input is required at this point of time when molding conditions and screw-related data, for example, are already registered. After the completion of the processing to input the basic data Do, the existence of data misinput or input omission, for example, is confirmed to turn ON a confirmation key (not shown) (Step S5).

As a result, the solid phase rate calculation processing unit Fcp performs calculation processing based on the inputted basic data Do and the solid phase rate calculation formula data Dc (Step S6). This calculation processing calculates the estimated solid phase rate Xcs based on the basic data Do. Thus, the resultant estimated solid phase rate Xcs is at least temporarily registered in the internal memory 21*m* (Step S7). The decomposition rate calculation processing unit Fcr also performs calculation processing based on the inputted basic data Do and the decomposition rate calculation formula data Dr (Step S8). This calculation processing calculates the estimated resin decomposition rate Xrs based on the basic data Do. Thus, the resultant estimated resin decomposition rate Xrs is at least temporarily registered in the internal memory 21*m* (Step S9).

After the estimated solid phase rate Xcs and the estimated resin decomposition rate Xrs are obtained, the determination processing unit Fcj performs, based on the criterion shown in FIG. 7, determination processing to determine the levels of the estimated solid phase rate Xcs and the estimated resin decomposition rate Xrs (Step S10). Then, based on the result of the determination processing, the support messages mr, m1, m2, and m3 shown in FIG. 7 corresponding to this result are selected to output the support message data Dh corresponding to the selected support message mr . . . (Step S11).

On the other hand, the output processing function unit Fd selects, in Step S11, the selected support message mr, m1, m2, or m3 shown in FIG. 8*a*-FIG. 8*d* based on the support message data Dh outputted from the determination processing unit Fcj to display the selected message on the message display unit 5*d* (Step S12).

When the message display unit 5*d* displays the support message m1, m2, or m3 other than the suitable message mr, processing to change the molding conditions is performed based on the displayed support message m1, m2, or m3 (i.e., the determination message m1*j* . . . and the countermeasure message m1*p* . . . ) (Step S13,S14). For example, when the support message m2 (the determination message m2*j*, the countermeasure message m2*p*) is displayed, the setting may be changed in order to increase one or two or more of the set temperature Ts, the backpressure Pr, and the rotation number Rm and the setting may be changed to increase the cycle time Ct based on the message that: "There is a possibility of un-melted resin" (determination message m2*j*), and the message: "Please increase Ts, Pr, and Rm or increase the length of Ct" (countermeasure message m2*p*).

In this case, the level change may be performed based on the judgement by the operator. The operator is allowed, as described above, to confirm the numerical value display or the graphic display, for example, of the estimated solid phase rate Xcs and the estimated resin decomposition rate Xrs in a more visual manner so that the operator can confirm any level deviating from a suitable range and thus can judge how much the level of the molding conditions should be changed.

After the completion of the processing to change the molding conditions, a reprocessing key (not shown) is turned ON to thereby perform a recalculation processing to recalculate the estimated solid phase rate Xcs and the estimated resin decomposition rate Xrs and a redetermination processing is performed (Steps S15, S6 . . . ).

On the other hand, when the message display unit 5*d* displays the suitable message mr in Step S12, the molten state is sufficient and no deterioration state is found, thus leading to the confirmation of a preferred molding environment. Thus, the processing can proceed to the next step to turn ON an end key (not shown) and complete the execution of the support program Ps (Steps S13 and S16). Specifically, the use of the molding support device 1 can be completed.

Figure 10:
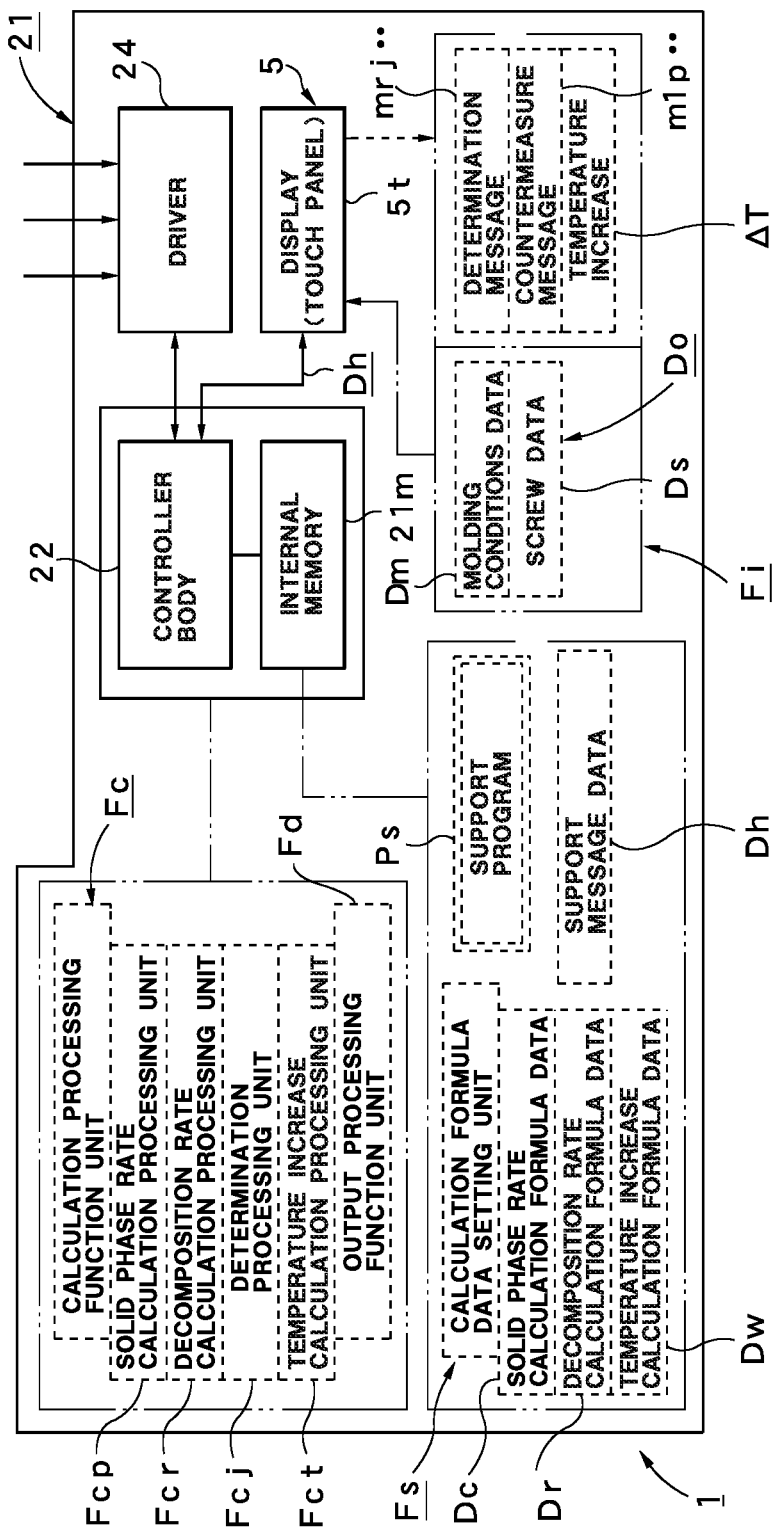
FIG. 10 is a block system diagram according to a modification example of the molding support device.
Figure 11:
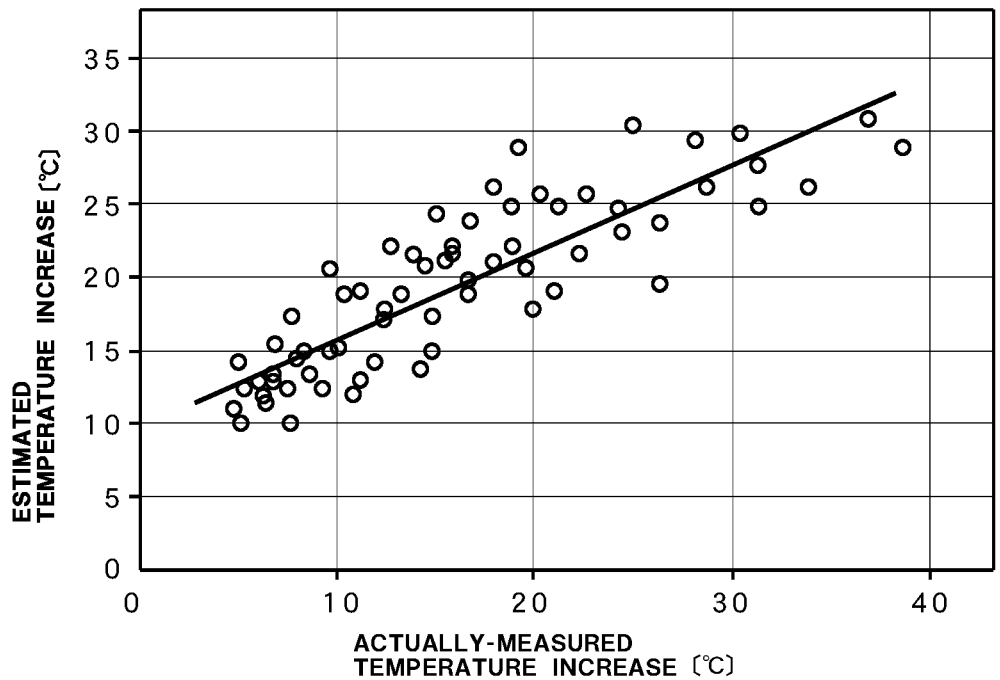
FIG. 11 is a correlation characteristic diagram illustrating the relation between an estimated temperature increase in the modification example of the molding support device and an actually-measured temperature increase.
Figure 12:
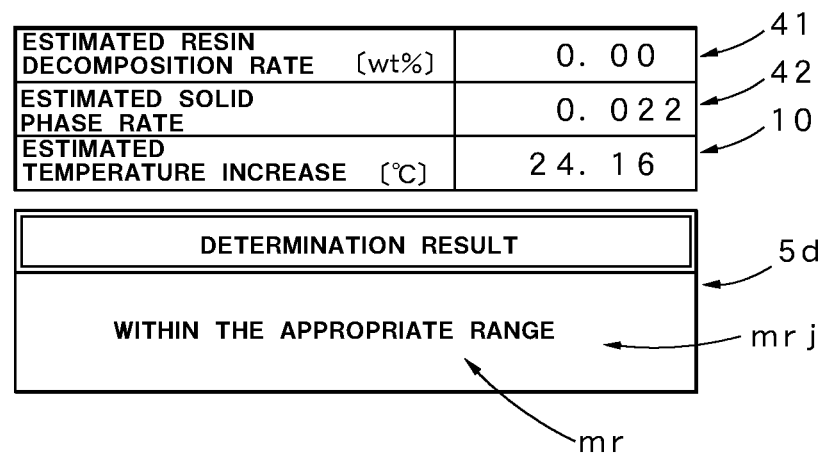
FIG. 12 illustrates the display screen of a temperature increase display unit in the modification example of the molding support device.

Next, the following section will describe a modification example of the molding support device 1 of this embodiment with reference to FIG. 10-FIG. 12.

The solid phase rate Xc and the resin decomposition rate Xr also have a close relation with the temperature increase of resin. Thus, regarding the above-described information for the estimated solid phase rate Xcs and the estimated resin decomposition rate Xrs, the estimated temperature increase $\Delta T$ can be displayed as information related to the resin molten state to allow the operator (user) to appropriately grasp the molten state more appropriately.

Thus, the molding support device 1 is configured as shown in FIG. 10 so that the above-described calculation formula data setting unit Fs sets the temperature increase calculation formula data Dw based on data related to shearing heating value E used for the calculation processing by the resin decomposition rate calculation formula data Dr. The calculation processing function unit Fc includes the temperature increase calculation processing unit Fct that calculates the estimated temperature increase $\Delta T$ by means of the calculation processing based on the temperature increase calculation formula data Dw. The output processing function unit Fd includes the temperature increase display unit 10 to allow the display 5 to display the estimated temperature increase ΔT calculated by the temperature increase calculation processing unit Fct.

One example of the temperature increase calculation formula that is the foundation of the temperature increase calculation formula data Dw is shown in [formula 103].

Estimated temperature increase $\Delta T = E/(Q \cdot Cm)$ [formula 103]

In [formula 103], E[MJ] can use the shearing heating value E in [formula 102] to calculate the above-described resin decomposition rate Xr. As described above, the estimated temperature increase ΔT can be calculated using the above-described data related to shearing heating value E used for the calculation processing by the resin decomposition rate calculation formula data Dr also for the calculation processing of the temperature increase calculation formula data Dw, thus advantageously providing easy calculation of the estimated temperature increase ΔT. The reference numeral Q denotes the plasticizing capacity and the reference numeral Cm denotes a melting specific heat capacity (resin specific heat capacity). Specifically, the estimated temperature increase ΔT can be calculated by dividing the shearing heating value E from the fully-melted position to the screw tip end by the plasticizing capacity Q and the resin specific heat capacity Cm. The molten resin was handled not as Newtonian liquid such as water, but as index fluid such as starch syrup. FIG. 11 illustrates the relation between the estimated temperature increase ΔT and the actually-measured temperature increase by the correlation characteristic. This characteristic uses ABS resin as resin. The estimated temperature increase ΔT is always lower than the critical value p=0.01, thus showing a sufficient correlation.

FIG. 12 illustrates one example of the display screen of the temperature increase display unit 10 in the modification example. The illustrated temperature increase display unit 10 is displayed together with the message display unit 5d at the upper side of the message display unit 5d. In addition to the temperature increase display unit 10 that displays the calculation value of this estimated temperature increase ΔT, further provided are the resin decomposition rate display unit 41 that displays the calculation value of the estimated resin decomposition rate Xrs and the solid phase rate display unit 42 that displays the calculation value of the estimated solid phase rate Xcs. As described above, the output processing function unit Fd has the temperature increase display unit 10 to allow the display 5 to display the estimated temperature increase ΔT calculated by the temperature increase calculation processing unit Fct. This allows the information related to the estimated solid phase rate Xcs and/or the estimated resin decomposition rate Xrs and the information related to the estimated temperature increase ΔT to be collectively confirmed visually, thus advantageously showing the resin molten state more appropriately. In FIG. 10-FIG. 12, the same parts as those of FIG. 1-FIG. 9 are denoted with the same reference numerals to clarify the configuration and will not be further described.

As described above, the best embodiment has been described in detail. However, the present invention is not limited to such an embodiment and can be subjected to arbitrary change, addition, or deletion with regard to the detailed configuration, shape, material, quantity, numerical value, or method for example within a scope not deviating from the intention of the present invention.

For example, the molding conditions data Dm and the screw data Ds have been illustrated as the basic data Do. However, other pieces of data may be used or a part of the illustrated data may be used. The touch panel 5t of the display 5 has been illustrated as the basic data input unit Fi. However, various input means may be used as the basic data input unit Fi for a case wherein data of an external memory storing the basic data Do is transferred or is sent by transmission means, or all data is registered in the internal memory 21m in advance to select the basic data Do from the data, for example. On the other hand, the solid phase rate calculation formula data Dc and the decomposition rate calculation formula data Dr are one example and do not exclude other pieces of calculation formula data based on which the solid phase rate Xc and the resin decomposition rate Xr can be calculated. The values and contents of the support messages mr, m1, and m2 . . . are an example. Thus, various other messages may be used.

INDUSTRIAL APPLICABILITY

The molding support device according to the present invention can be used for various injection molding machines to inject plasticized molten resin with a screw to fill a metal mold with the resin to perform a molding operation.

The invention claimed is:

1. A molding support device for an injection molding machine for performing a molding support to an injection molding machine to inject plasticized molten resin with a screw to fill a metal mold with the resin, the molding support device comprising:
a basic data input unit that inputs basic data including molding conditions data related to at least molding conditions and screw data related to the form of the screw;
a calculation formula data setting unit that sets solid phase rate calculation formula data to calculate, based on this basic data, the solid phase rate of the molten resin in the heating cylinder;
a calculation processing function unit that has a solid phase rate calculation processing unit to use calculation processing based on the basic data and the solid phase rate calculation formula data to calculate an estimated solid phase rate of the molten resin at the measurement completion; and
an output processing function unit that performs display processing to display information related to the estimated solid phase rate on a display,
wherein the screw data includes data relating to the type of material of a surface of the screw; and
wherein the calculation formula data setting unit sets decomposition rate calculation formula data to calculate the resin decomposition rate of the screw surface during a molding operation based on the basic data.

2. The molding support device for the injection molding machine according to claim 1, wherein: the molding conditions data includes data related to the type of resin material to be used.

3. The molding support device for the injection molding machine according to claim 1, wherein: the calculation processing function unit has a decomposition rate calculation processing unit to use calculation processing based on the basic data and the decomposition rate calculation formula data to calculate an estimated resin decomposition rate.

4. The molding support device for the injection molding machine according to claim 3, wherein: the calculation processing function unit includes a determination processing unit to perform determination processing to determine the level(s) of the estimated solid phase rate and/or the estimated resin decomposition rate to output support message data corresponding to the result of the determination processing.

5. The molding support device for the injection molding machine according to claim 4, wherein: the output processing function unit has a function to allow a message display unit of the display to display a support message based on the support message data outputted from the determination processing unit.

6. The molding support device for the injection molding machine according to claim 5, wherein: the support message includes a determination message showing the result of the determination processing and a countermeasure message to provide a countermeasure to this determination message.

7. The molding support device for the injection molding machine according to claim 1, wherein: the calculation formula data setting unit sets temperature increase calculation formula data to calculate an estimated temperature increase based on data related to a shearing heating value used for a calculation processing based on the resin decomposition rate calculation formula data.

8. The molding support device for the injection molding machine according to claim 7, wherein: the calculation processing function unit includes a temperature increase calculation processing unit to use calculation processing based on the temperature increase calculation formula data to calculate an estimated temperature increase.

9. The molding support device for the injection molding machine according to claim 8, wherein: the output processing function unit includes a temperature increase display unit to allow the display to display the estimated temperature increase calculated by the temperature increase calculation processing unit.

* * * * *